(12) United States Patent
Hirochika et al.

(10) Patent No.: US 7,067,717 B2
(45) Date of Patent: Jun. 27, 2006

(54) ISOLATED GENE CONTROLLING DISEASE RESISTANCE ACTIVITY IN PLANTS AND USE THEREOF

(75) Inventors: Hirohiko Hirochika, Ibaraki (JP); Akio Miyao, Ibaraki (JP); Katsura Onosato, Tokyo (JP)

(73) Assignees: National Institute of Agrobiological Sciences, Ibaraki (JP); Bio Oriented Technology Research Advancement Institution, Saitama (JP)

( * ) Notice: Subject to any disclaimer, the term of this patent is extended or adjusted under 35 U.S.C. 154(b) by 267 days.

(21) Appl. No.: 10/304,339

(22) Filed: Nov. 26, 2002

(65) Prior Publication Data

US 2004/0003428 A1    Jan. 1, 2004

(30) Foreign Application Priority Data

May 24, 2002  (JP) .............................. 2002-151627

(51) Int. Cl.
  *C12N 15/09* (2006.01)
  *C12N 15/29* (2006.01)
  *C12N 15/82* (2006.01)
  *A01H 5/00* (2006.01)
  *A01H 5/10* (2006.01)

(52) U.S. Cl. ...................... 800/279; 800/278; 800/298; 800/295; 435/320.1; 435/468; 536/23.6

(58) Field of Classification Search ................ 800/279, 800/278, 320.2, 298, 295; 435/320.1, 468; 536/23.6
See application file for complete search history.

(56) References Cited

U.S. PATENT DOCUMENTS 5,952,485 A * 9/1999 Ronald et al. ............. 536/23.6
6,074,877 A * 6/2000 D'Halluin et al. .......... 435/468

FOREIGN PATENT DOCUMENTS

WO    WO 01/18061 A2    3/2001

OTHER PUBLICATIONS

Lazar et al (Molecular and Cellular Biology, Mar. 1988, vol. 8, No. 3, pp. 1247-1252.*
Broun et al. Science, Nov. 13, 1998, vol. 282, pp. 131-137.*
Zhou et al. Cell, vol. 83, pp. 925-935 (1995).*

* cited by examiner

*Primary Examiner*—Medina A. Ibrahim
(74) *Attorney, Agent, or Firm*—Jacqueline F. Mahoney; Perkins Coie LLP (57) ABSTRACT

A polynucleotide encoding a plant gene capable of controlling disease resistance reactions in plants is provided which includes a polynucleotide having a nucleotide sequence encoding amino acid sequence from methionine at position 1 to Serine at position 361 of SEQ ID NO: 2 in the sequence listing, or having the amino acid sequence having one or several amino acid deletions, substitutions and/or additions, and being capable of controlling disease resistance reactions.

12 Claims, 4 Drawing Sheets

FIG. 1

Wild type     Mutant type

FIG.2

```
   1 ACACACGCTG TGCTGCTGCT GCTGCCGCTG CTCCTCCTCC TCCTCTTACA
  51 TCCCATCCTC GCCGCGATTT CCTTCGCCGC CGCCGCCGGC TTCGTCTTCT
 101 TCCCCGGCGC CGGGGCACGC GAAAAGGGTT TGTTTCTAGT AGAATATGTC
 151 GTGCTTTGCA TGCTGTGGTG ATGAAGATAC TCAAGGAGTA CCAGACAACA
 201 GGAATCCATA CCCAGGGAAC CATCCAGCAA GGAGCGATGC ATATCGCACA
 251 GCTGATCCAA CTCCAAGAGG TCCTCAACCT GTGAAAGTGC AACCAATTGC
 301 AGTCCCCATC ATTCCTGTTG ATGAAATTAG GAAGTGACT AAGAATTTTG
 351 GTGATGAAGC TTTGATTGGT GAAGGTTCCT TTGGCAGAGT GTATTTTGGT
 401 GTTCTAAGAA ATGGTAGAAG TGCAGCGGTC AAAAAGCTAG ACTCTAGTAA
 451 GCAGCCAGAC CAAGAATTTT TGGCACAGGT ATCTATGGTG TCGAGGCTTA
 501 AGCATGAACA TGTTGTTGAG CTGCTTGGTT ATTGTGTTGA TGGAAATCTC
 551 CGTGTCCTTG CTTATGAGTT TGCGACTATG GGTTCTCTTC ATGATATGCT
 601 TCATGGAAGG AAGGGTGTTA AAGGAGCTCA ACCTGGTCCA GTCTTATCAT
 651 GGGCACAACG TGTGAAGATA GCTGTTGGGG CAGCAAAAGG CCTGGAGTAT
 701 CTTCATGAGA AAGCACAGCC TCATATCATA CACAGGGACA TCAAGTCCAG
 751 CAATGTTCTC CTTTTCGATG ATGATGTTGC TAAAATAGCT GACTTTGATT
 801 TGTCAAACCA AGCTCCTGAC ATGGCAGCTC GGCTTCACTC TACTAGGGTT
 851 CTTGGAACCT TTGGATATCA TGCACCTGAG TATGCAATGA CTGGACAGCT
 901 TAGCTCCAAG AGTGATGTGT ACAGTTTTGG AGTTGTTCTT CTTGAGCTAT
 951 TGACCGGAAG GAAACCTGTT GACCATACAT TACCAAGGGG ACAGCAGAGT
1001 CTTGTGACTT GGGCCACCCC AAGGCTTAGT GAAGACAAGG TTAGGCAATG
1051 TGTTGACTCA AGACTTGGAG GGGACTATCC TCCTAAAGCT GTCGCAAAGT
1101 TTGCAGCTGT TGCGGCGTTA TGCGTTCAGT ATGAAGCGGA CTTTCGACCA
1151 AACATGAGCA TTGTCGTGAA AGCGCTGCAA CCCCTGCTGA ATGCTCGGGC
1201 AACTAACCCT GGAGAAAATG CCGGGTCATA AAACTTTGGT CTACCTTTTG
1251 TATGATAGAT ATTAAGTTAA GAAGTATGAG ACATCGATAT TGTTCTTGCG
1301 GATGTGTGGC TGGCTGGAAG TGTGTACATT TGTGATTATT CGTCCCTTGT
1351 TGTAATCACC AAGGTTCTAG CAACCGAAAA TATTTGATTC TTCGC
```

FIG.3

| | | | | | | |
|---|---|---|---|---|---|---|
| Lesion mimic mutant causative gene | 1 | MSCFACCGDE | DTQGVPDNRN | PYPGNHPARS | DAYRTADPTP | RGPQPVKVQP |
| Pti1 (tomato) | 1 | MSCFSCCDDD | DWHRATDNGP | FMAHNSAGNN | GGQRATESAQ | RETQTVNIQP |
| Lesion mimic mutant causative gene | 51 | IAVPIIPVDE | IREVTKNFGD | EALIGEGSFG | RVYFGVLRNG | ESAAVKKLDS |
| Pti1 (tomato) | 51 | IAVPSIAVDE | LKDITDNFGS | KALIGEGSYG | RVYHGVLKSG | RAAAIKKLDS |
| Lesion mimic mutant causative gene | 101 | SKQPDQEFLA | QVSMVSRLKH | EHVVELLGYC | VDGNLRVLAY | EFATMGSLHD |
| Pti1 (tomato) | 101 | SKQPDREFLA | QVSMVSRLKD | ENVVELLGYC | VDGGFRVLAY | EYAPNGSLHD |
| Lesion mimic mutant causative gene | 151 | MLHGRKGVKG | AQPGPVLSWA | QRVKIAVGAA | KGLEYLHEKA | QPHIIHRDIK |
| Pti1 (tomato) | 151 | ILHGRKGVKG | AQPGPVLSWA | QRVKIAVGAA | KGLEYLHEKA | QPHIIHRDIK |
| Lesion mimic mutant causative gene | 201 | SSNVLLFDDD | VAKIADFDLS | NQAPDMAARL | HSTRVLGTFG | YHAPEYANTG |
| Pti1 (tomato) | 201 | SSNMLLFDDD | VAKIADFDLS | NQAPDMAARL | HSTRVLGTFG | YHAPEYANTG |
| Lesion mimic mutant causative gene | 251 | QLSSKSDVYS | FGVVLLELLT | GRKPVDHTLP | RGQQSLVTWA | TPRLSEDKVR |
| Pti1 (tomato) | 251 | QLSSKSDVYS | FGVVLLELLT | GRKPVDHTLP | RGQQSLVTWA | TPRLSEDKVK |
| Lesion mimic mutant causative gene | 301 | QCVDSRLGGD | YPPKAVAKFA | AVAALCVQYE | ADFRPNMSIV | VKALQPLLNA |
| Pti1 (tomato) | 301 | QCVDARLNTD | YPPKAIAKWA | AVAALCVQYE | ADFRPNMSIV | VKALQPLLPE |
| Lesion mimic mutant causative gene | 351 | RATNPGENAG | S | | | |
| Pti1 (tomato) | 351 | PYPS | | | | |

ISOLATED GENE CONTROLLING DISEASE RESISTANCE ACTIVITY IN PLANTS AND USE THEREOF

BACKGROUND OF THE INVENTION

1. Field of the Invention

The present invention relates to a novel gene. More particularly, the present invention relates to a novel gene encoding a protein capable of controlling disease resistance reactions in plants.

2. Description of the Related Art

A number of gene disruption strains of rice have been produced by the property of rice retrotransposon Tos17 that it is activated by cell/tissue culture to undergo transposition. Transposons are mutagenic genes which are ubiquitous in the genomes of animals, yeast, bacteria, and plants. Transposons are classified into two categories according to their transposition mechanism. Transposons of class II undergo transposition in the form of DNA without replication. Examples of class II transposons include Ac/Ds, Spm/dSpm and Mu elements of maize (*Zea mays*) (Fedoroff, 1989, Cell 56, 181–191; Fedoroff et al., 1983, Cell 35, 235–242; Schiefelbein et al., 1985, Proc. Natl. Acad. Sci. USA 82, 4783–4787), and Tam element of [*Antirrhinum* (*Antirrhinum majus*) (Bonas et al., 1984, EMBO J, 3, 1015–1019). Class II transposons are widely used for gene isolation by means of transposon tagging. Such a technique utilizes a property of transposons, that is, a transposon transposes within a genome and enters a certain gene and, as a result, such a gene is physiologically and morphologically modified, whereby the phenotype controlled by the gene is changed. If such a phenotype change can be detected, the affected gene may be isolated (Bancroft et al., 1993, The Plant Cell, 5, 631–638; Colasanti et al., 1998, Cell, 93, 593–603; Gray et al., 1997, Cell, 89, 25–31; Keddie et al., 1998, The Plant Cell, 10, 877–887; and Whitham et al., 1994, Cell, 78, 1101–1115).

Transposons of class I are also called retrotransposons. Retrotransposons undergo replicative transposition through RNA as an intermediate. A class I transposon was originally identified and characterized in Drosophila and yeast. A recent study has revealed that retrotransposons are ubiquitous and dominant in plant genomes (Bennetzen, 1996, Trends Microbiolo., 4, 347–353; Voytas, 1996, Science, 274, 737–738). It appears that most retrotransposons are an integratable but non-transposable unit. Recently, it has been reported that some retrotransposons of such a type are activated under stress conditions, such as injury, pathogen attack, and cell culture (Grandbastien, 1998, Trends in Plant Science, 3, 181–187; Wessler, 1996, Curr. Biol., 6, 959–961; Wessler et al., 1995, Curr. Opin. Genet. Devel., 5, 814–821). For example, such activation under stress conditions was found in retrotransposons of tobacco, Tnt1A and Tto1 (Pouteau et al., 1994, Plant J., 5, 535–542; Takeda et al., 1988, Plant Mol. Biol., 36, 365–376), and a retrotransposon of rice, Tos17 (Hirochika et al., 1996, Proc. Natl. Acad. Sci. USA, 93, 7783–7788).

The rice retrotransposon Tos17 is a class I element in plants which has been extensively studied. Tos17 was cloned by RT-PCR using degenerate primers which had been prepared based on a conserved amino acid sequence of the reverse transcriptase domains of Ty1-copia group retroelements (Hirochika et al., 1992, Mol. Gen. Genet., 233, 209–216). Tos17 has a length of 4.3 kb and has two identical LTRs (long terminal repeats) of 138 bp and a PBS (primer binding site) which is complementary to the 3' end of the initiator methionine tRNA (Hirochika et al., 1996, supra). Transcription of Tos17 is strongly activated by tissue culture, and the copy number of Tos17 increases with time in culture. Its initial copy number in Nipponbare (a Japonica variety), which is used as a genome research model, is two. In plants regenerated from tissue culture, its copy number is increased to 5 to 30 (Hirochikaet al., 1996, supra). Unlike class II transposons found in yeast and *Drosophila*, Tos17 undergoes random transposition in a chromosome and induces mutation in a stable manner. Therefore, Tos17 provides a useful tool in reverse genetics for analyzing the function of a gene in rice (Hirochika, 1997, Plant Mol. Biol. 35, 231–240; K. Shimamoto Ed., 1999, Molecular Biology of Rice, Springer-Verlag, 43–58).

SUMMARY OF THE INVENTION

The present inventors have found a lesion mimic mutant among a number of rice gene disruption strains by utilizing the property of rice retrotransposon Tos17 that it is activated by culture to undergo transposition. This mutant develops brown spots on its leaves as if it is infected with a pathogen. The brown spots spread throughout the leaves and the plant eventually wilts. The inventors rigorously studied the relationship between the alteration of the property and disease resistance. As a result, it was found that a gene causing the property alteration is involved in disease resistance reactions, whereby the present invention was completed.

According to one aspect of the present invention, a polynucleotide is provided, which encodes a plant gene capable of controlling disease resistance reactions in plants. The polynucleotide includes a polynucleotide having a nucleotide sequence encoding amino acid sequence from methionine at position 1 to Serine at position 361 of SEQ ID NO: 2 in the sequence listing, or having the amino acid sequence having one or several amino acid deletions, substitutions and/or additions, and being capable of controlling disease resistance reactions.

According to another aspect of the present invention, a polynucleotide is provided, which encodes a plant gene capable of controlling disease resistance reactions inplants. The polynucleotide includes i) a nucleotide sequence from A at position 146 to A at position 1231 in SEQ ID NO: 1 in the sequence listing, or ii) a nucleotide sequence hybridizable to the nucleotide sequence of i) under stringent conditions.

In one embodiment, the disease resistance reaction can be controlled by induction of expression of a defense-related gene.

In one embodiment, the polynucleotide is derived from rice.

According to another aspect of the present invention, a vector is provided, which contains the polynucleotide which is operably linked to a control sequence.

According to another aspect of the present invention, a method is provided for controlling disease resistance reactions in plants, which comprises the step of introducing the above-described polynucleotide into the plant.

Thus, the invention set forth herein makes possible the advantages of providing a novel plant gene using Tos17, more particularly, a plant gene capable of controlling disease resistance reactions in plants; a vector containing the gene; a plant transformed with the gene; and a method for improving a plant comprising the step of introducing the gene into a plant.

These and other advantages of the present invention will become apparent to those skilled in the art upon reading and understanding the following detailed description with reference to the accompanying figures.

BRIEF DESCRIPTION OF THE DRAWINGS

FIG. 2 is a diagram showing the base sequence of cDNA of the causative gene of the lesion mimic mutant (SEQ ID NO:1).

DESCRIPTION OF THE PREFERRED EMBODIMENTS

The present invention provides a novel plant gene which has been isolated using Tos17 and whose function has been clarified.

The term "gene" as used herein refers to a structural unit carrying hereditary information and an element defining a trait. A gene may be defined as a hereditary functional unit specified by the base sequence of a certain region in polymer DNA or RNA. Therefore, a gene may be understood as a DNA or RNA which will be eventually translated into a protein, or a polynucleotide.

The present invention provides a polynucleotide encoding a plant gene capable of controlling disease resistance reactions in plants. The term "disease resistance" as used herein refers to capability for defending against the attack of a pathogen causing disease in plants. Examples of the pathogen include viroids, viruses, mycoplasma-like microorganism (phytoplasma), bacteria, fungi, protozoa, nematodes, and parasitic plants. The term "capable of controlling disease resistance reactions" as used herein indicates that the disease resistance can be raised or promoted.

The mechanism of disease resistance in plants has been studied. A series of defense reactions are actively raised in plant cells and tissue against the attack of enemies including known defense reactions below: i) generation of active oxygen and initiation of a hyper-sensitive reaction in association therewith; and ii) expression of a defense-related gene. The expression of the defense-related gene leads to induction of expression of genes involved in synthesis of isoflavonoid phytoalexin, such as phenylpropanoid synthase (e.g., phenylalanine ammonialyase (PAL), caffeic acid dehydrogenase) or chalcone synthase (CHS) and accumulation of the gene products, or induction of expression of genes involved in synthesis of terpene phytoalexin, such as HMG-CoA-reducing enzyme and accumulation of the gene products; and synthesis of PR proteins which decompose the cell wall of invading bacteria, releasing an elicitor molecule from the invading bacteria or the cell wall of the plant. The polynucleotide of the present invention may be involved in the reactions described in i) and ii). Examples of the defense-related gene include genes encoding pathogenesis-related protein 1b (PR1b) and phenylalanine ammonialyase (PAL). Phytoalexin is an antibacterial substance which is synthesized or activated by host plant cells into which enemies (including parasites) invade. Examples of the phytoalexin include momilactone A and sakuranetin.

The polynucleotide of the present invention as mentioned above is a polynucleotide, including a polynucleotide having a nucleotide sequence encoding an amino acid sequence from methionine (Met) at position 1 to serine (Ser) at position 361 in SEQ ID NO: 2 in the sequence listing, or a nucleotide sequence having the amino acid sequence having one or several amino acid deletions, substitutions, and/or additions. In one embodiment, the polynucleotide of the present invention is a polynucleotide having a nucleotide sequence at position 146–1231 of SEQ ID NO: 1 of the sequence listing. The polynucleotide of the present invention may further contain a nucleotide sequence (e.g., a non-translational region) out of (to the 5' or 3' terminus) the above-described regions (the nucleotide sequence region encoding the amino acid sequence from methionine (Met) at position 1 to Serine (Ser) at position 361 of SEQ ID NO: 2 or the nucleotide sequence region at position 146–1231 of SEQ ID NO: 1). More preferably, the polynucleotide of the present invention consists of the full-length sequence at position 1–1395 of SEQ ID NO: 1. The polynucleotide of the present invention includes all degenerate isomers of SEQ ID NO: 1. The term "degenerate isomer" refers to DNA encoding the same polypeptide and having a degenerate codon(s). For example, for a DNA having the base sequence of SEQ ID NO: 1 in which a codon corresponding to a certain amino acid (e.g., Asn) thereof is AAC, a DNA in which the AAC is changed to the degenerate codon AAT is called a degenerate isomer.

The polynucleotide of the present invention has been obtained from a rice genomic DNA using Tos17 as a marker based on the finding of a lesion mimic mutant of a rice gene disruption strain produced using the property of rice retrotransposon Tos17 that it is activated by culture and undergoes transposition. Therefore, in one embodiment, the polynucleotide of the present invention is derived from rice.

Fragments and variants of the disclosed nucleotide sequences and proteins encoded thereby may be included in the present invention. The term "fragment" is intended to refer to a portion of a nucleotide sequence or a portion of an amino acid sequence, or a protein encoded thereby. A fragment of a nucleotide sequence may encode a protein fragment holding at least one functional biological activity of a native protein.

A variant of a protein encoded by the polynucleotide of the present invention is intended to refer to a protein modified from the native protein by at least one amino acid deletion (truncation) or addition at the N and/or C terminus of the protein; at least one amino acid deletion or addition at at least one site in the protein; or at least one amino acid substitution at at least one site in the protein. Such a variant may be generated by genetic polymorphism or artificial modification, for example.

The protein encoded by the polynucleotide of the present invention may be modified using various methods (including amino acid substitution, deletion, truncation, and insertion). These methods are generally known in the art. For example, a variant of the amino acid sequence of the protein encoded by the plant gene capable of controlling disease resistance reactions of the present invention may be prepared by mutagenesis. Methods for mutagenesis and modification of a nucleotide sequence are known in the art, e.g., Kunkel (1985) Proc. Natl. Acad. Sci. USA 82:488–492; Kunkel et al. (1987) Methods in Enzymol. 154:367–382; U.S. Pat. No. 4,873,192; Walker and Gaastra ed. (1983) Techniques in Molecular Biology (MacMillian Publishing Company, New York) and their cited references. Guidance as to appropriate amino acid substitutions that do not affect biological activity of the protein of interest may be found in themodel of Dayhoff et al. (1987) Atlas of Protein Sequence and Structure (Natl. Biomed. Res. Found. Washington, D.C.), which is herein incorporated by reference. Conservative substitution (e.g., one amino acid is substituted with another one having a similar property) may be preferable. Examples of such a substitution include a substitution between hydrophobic amino acids (Ala, Ile, Leu, Met, Phe, Pro, Trp, Tyr, and Val); a substitution between hydrophilic amino acids (Arg, Asp, Asn, Cys, Glu, Gln, Gly, His, Lys, Ser, and Thr); a substitution between amino acids having an aliphatic side chain (Gly, Ala, Val, Leu, Ile, and Pro); a substitution between amino acids having a side chain containing a hydroxyl group (Ser, Thr, and Tyr); a substitution between amino acids having a side chain containing a sulfur atom (Cys and Met); a substitution between amino acids having a side chain containing carboxylic acid and amide (Asp, Asn, Glu, and Gln); a substitution between amino acids having a side chain containing a base (Arg, Lys, and His); and a substitution between amino acids having a side chain containing an aromatic compound (His, Phe, Tyr, and Trp).

Therefore, "one or several deletions, substitutions and/or additions" refers to as many amino acid substitution(s), deletion(s) and/or addition(s) as those caused by genetic polymorphism or artificial modification (including the above-described well-known methods). "One or several deletions, substitutions and/or additions" are any number of amino acid deletions, additions, and/or substitutions as long as a gene having such modifications still has the function of the protein encoded by the polynucleotide of the present invention. It will be clearly understood by those skilled in the art that the influence of modifications (amino acid substitutions, deletions and/or additions) on activity may be dependent on the positions, extent, types, or the like of amino acids to be modified. The polynucleotide of the present invention may have as many deletions, substitutions and/or additions in the full-length amino acid sequence as those which allow the polynucleotide to still have amino acid sequence identity defined below, as long as the function of the protein encoded by the polynucleotide of the present invention can be expressed, for example.

The polynucleotide encoding the plant gene capable of controlling disease resistance reactions of the present invention includes a polynucleotide having a nucleotide sequence encoding an amino acid sequence having at least 60% sequence identity to the amino acid sequence from Met at position 1 to Ser at position 361 in SEQ ID NO: 2 of the sequence listing as long as it can similarly control disease resistance reactions, preferably at least 65%, more preferably at least 70%, more preferably at least 75%, even more preferably at least 80%, still more preferably at least 90%, still even more preferably at least 95%, and most preferably at least 99%.

The polynucleotide encoding the plant gene capable of controlling disease resistance reactions of the present invention includes a polynucleotide having a nucleotide sequence having at least 70% sequence identity to the nucleotide sequence (preferably, a nucleotide sequence from A at position 146 to A at position 1231 in SEQ ID NO: 1) encoding the amino acid sequence from Met at position 1 to Ser at position 361 in SEQ ID NO: 2 of the sequence listing as long as it can similarly control disease resistance reactions, preferably at least 75%, more preferably at least 80%, even more preferably at least 85%, still more preferably at least 90%, still even more preferably at least 95%, and most preferably at least 99%.

As used herein, a "reference sequence" refers to a defined sequence used as a basis for a sequence comparison. A reference sequence may be a subset or the whole of the specified sequence: for example, a segment of a full-length cDNA or gene sequence or a complete DNA or gene sequence.

As used herein, a "comparison window" includes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those skilled in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Global optimal alignment of a reference sequence (the sequence of the present invention) and a subject sequence is preferably determined by homology analysis using BLAST (Altshul et al., 1997, Nucleic Acids Res., 25,3389–3402). In a sequence alignment, the reference and subject sequences are both DNA sequences. An RNA sequence can be compared by converting U's to T's. The result of the global sequence alignment is in percent identity. The sequence alignment may be conducted using default parameters in the program.

As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted with other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those skilled in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated with, e.g., the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. Those skilled in the art will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90%, and most preferably at least 95%.

The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Optionally, optimal alignment is conducted using the homology alignment algorithm of Needleman et al., J. Mol. Biol. 48: 443(1970). A peptide is substantially identical to a second peptide, for example, where the two peptides differ only by a conservative substitution. Peptides which are "substantially similar" share sequences as noted above except that residue positions which are not identical may differ by conservative amino acid changes.

Fragments of the plant gene nucleotide sequence of the present invention capable of controlling disease resistance reactions, which encode a biologically active portion of a protein capable of controlling disease resistance reactions, encode at least 15, 25, 30, 50, 100, 125, 150, 175, 200, or 225 contiguous amino acids, or the overall amino acids present in the full-length protein of the present invention (e.g., 361 amino acids of SEQ ID NO: 2). In general, a fragment of the plant gene nucleotide sequence capable of controlling disease resistance reactions, which is used as a PCR primer or a hybridization probe, may not encode a biologically active portion of a protein capable of controlling capable of disease resistance reactions in plants.

Polynucleotides encoding a plant gene capable of controlling disease resistance reactions derived from plants other than rice may be included in the scope of the present invention. Such a polynucleotide may be isolated by, for example, conducting PCR using a primer designed based on the full-length or a portion of a disclosed nucleotide sequence and the genomic DNA of a selected plant as a template, followed by screening genomic DNA or cDNA libraries of the same plant using an obtained amplified DNA fragment as a probe. In this manner, methods such as PCR, hybridization, and the like can be used to identify such sequences based on their sequence identity to the sequence set forth herein. Sequences isolated based on their sequence identity to the sequences set forth herein or to fragments thereof are encompassed by the present invention.

In a hybridization technique, all or part of a known nucleotide sequence can be used as a probe which selectively hybridizes a nucleotide sequence present in a group of cloned genomic DNA fragments or cDNA fragments derived from a selected organism (i.e., genomic libraries or cDNA libraries). The hybridization probe may be genomic DNA fragments, cDNA fragments, RNA fragments, or other oligonucleotides, and may be labeled with a detectable group (e.g., $^{32}$p) or any other detectable marker. Therefore, probes for hybridization can be made by labeling synthetic oligonucleotides based on the nucleotide sequence of the plant gene capable of controlling disease resistance reactions in plants of the present invention. Methods for preparation of probes for hybridization and construction of cDNA libraries and genomic libraries are generally known in the art and are disclosed in Sambrook et al. (1989) Molecular Cloning: A Laboratory Manual (2nd ed., Cold Spring Harbor Laboratory Press, Plainview, N.Y., which is herein incorporated by reference).

For example, all or a part of a nucleotide sequence encoding the plant gene capable of controlling disease resistance reactions disclosed herein can be used as a probe hybridizable to the corresponding plant gene sequence capable of controlling disease resistance reactions and the messenger RNA thereof. To achieve specific hybridization under various condition, such a probe is unique to the plant gene sequence capable of controlling disease resistance reactions, and includes sequence having preferably at least about 10 nucleotides in length, and most preferably at least about 20 nucleotides in length. Such a probe can be used in PCR to amplify the plant gene sequence capable of controlling disease resistance reactions derived from a selected organism. Methods for PCR amplification are well known in the art (PCR Technology: Principles and Applications for DNA Amplification, H A Erlich ed., Freeman Press, New York, N.Y. (1992); PCR Protocols: A Guide to Methods and Applications, Innis, Gelfland, Snisky, and White ed., Academic Press, San Diego, Calif. (1990); Mattila et al. (1991) Nucleic Acids Res. 19: 4967; Eckert, K. A. and Kunkel, T. A. (1991) PCR Methods and Applications 1: 17; PCR, McPherson, Quirkes, and Taylor, IRL Press, Oxford, these are herein incorporated by reference). This technique can be used as a diagnostic assay to isolate additional encode sequences from a desired organism or to determine the presence of an encode sequence in an organism. The hybridization technique includes hybridization screening of plated DNA libraries (either plaques or colonys; e.g., Sambrook et al. (1989) Molecular Cloning: A Laboratory Manual (2nd ed., Cold Spring Harbor Laboratory Press, Plainview, N.Y.)).

The hybridization of the sequences may be conducted under stringent conditions. The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe. Alternatively, stringency conditions can be adjusted to allow some mismatching in sequences so that lower degrees of similarity are detected. Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) (pH 7.0 to 8.3) and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents (e.g., formamide). Exemplary stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary more stringent conditions include hybridization in 40 to 45% formamide, 1.0 M NaCl, 1% SDS at 37° C., and a wash in 0.5× to 1×SSC at 55 to 60° C. Exemplary even more stringent conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984), Anal. Biochem., 138: 267–284: $T_m=81.5°$ C.+16.6(log M)+0.41(% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with at least 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those skilled in the art will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen (1993), Laboratory Techniques in Biochemistry and Molecular Biology Hybridization with Nucleic Acid Probes Part I, Chapter 2 (Elsevier, N.Y.); and Ausubel, et al., Eds. (1995), Current Protocols in Molecular Biology, Chapter 2 (Greene Publishing and Wiley-Interscience, New York); Sambrook et al. (1989) Molecular Cloning: A Laboratory Manual (2nd ed., Cold Spring Harbor Laboratory Press, Plainview, N.Y., which is herein incorporated by reference).

The base sequence of the obtained gene can be determined by a nucleotide sequence analysis method known in the art or a commercially available automated sequencer.

The polynucleotide of the present invention is typically obtained in accordance with a method set forth herein, or may be obtained by chemical synthesis based on the sequences described in the present invention. For example, the polynucleotide of the present invention may be synthesized using a polynucleotide synthesizer commercially available from Applied BioSystems, Inc. (ABI) in accordance with the instructions provided by the manufacturer.

A desired property of the polynucleotide produced by the above-described genetic engineering method or chemical synthesis method, i.e., capability of controlling disease resistance reactions, can be confirmed by investigating expression of a defense-related gene in rice, in which the polynucleotide is used to express an antisense RNA, by Northern blotting analysis, in substantially the same manner as described in Example 9 below. The possession of a desired property of such a polynucleotide can also be confirmed by demonstrating that brown spot formation of variants is eliminated in a complementation test using lesion mimic mutants as obtained by transposition of Tos17, in accordance with substantially the same manner as described in Example 5 below.

The polynucleotide of the present invention may be used for production of a plant with resistance to various pathogens as well as a specific pathogen. Preferably, this plant is agriculturally useful. The development of such a disease resistant plant is expected to reduce agricultural loss due to the attack of pathogens.

A native or modified polynucleotide of the present invention may be ligated with an appropriate plant expression vector using a method well known to those skilled in the art, and the vector may be introduced into a plant cell using a known gene recombination technique. Preferably, it is expected to develop a plant, by introducing the polynucleotide of the present invention to the plant, so that a function of an endogenous gene is suppressed and disease resistance is obtained. The gene is incorporated in the DNA of a plant cell. Note that the DNA of a plant cell includes DNA contained in various organelles (e.g., mitochondria and chloroplasts) as well as chromosomes.

As used herein, a "plant expression vector" refers to a nucleic acid sequence to which various regulatory elements, such as a promoter which regulates expression of the gene of the present invention, are operatively linked in a host plant cell. The term "control sequence" as used herein refers to a DNA sequence having a functional promoter and any related transcription element (e.g., an enhancer, a CCAAT box, a TATA box, and a SPI site). The term "operably linked" as used herein indicates that a polynucleotide is linked to a regulatory element which regulates expression of a gene, such as a promoter or an enhancer, so that the gene can be expressed. The plant expression vector may preferably include plant gene promoters, terminators, drug-resistance genes, and enhancers. It is well known to those skilled in the art that the type of an expression vector and the type of a regulatory element used may be changed depending on the host cell. A plant expression vector used in the present invention may have a T-DNA region. The T-DNA region can enhance the efficiency of gene introduction, particularly when *Agrobacterium* is used to transform a plant.

The term "plant gene promoter" as used herein refers to a promoter which is expressed in plants. A plant promoter fragment can be employed which will direct expression of a polynucleotide of the present invention in all tissues of a regenerated plant. Examples of a promoter for structural expression include a promoter for nopaline synthase gene (Langridge, 1985, Plant Cell Rep. 4, 355), a promoter for producing cauliflower mosaic virus 19S-RNA (Guilley, 1982, Cell 30, 763), a promoter for producing cauliflower mosaic virus 35S-RNA (Odell, 1985, Nature 313, 810), rice actin promoter (Zhang, 1991, Plant Cell 3,1155), a maize ubiquitin promoter (Cornejo 1993, Plant Mol. Biol. 23, 567), and a REXϕ promoter (Mitsuhara, 1996, Plant Cell Physiol. 37, 49).

Alternatively, the plant promoter can direct expression of a polynucleotide of the present invention in a specific tissue or may be otherwise under more precise environmental or developmental control. Such promoters are herein referred to as "inducible" promoters. Examples of inducible promoters include promoters which are inducible by environmental conditions, such as light, low temperature, high temperature, dryness ultraviolet irradiation, or spray of a specific compound. Examples of such promoters include a promoter for a gene encoding ribulose-1,5-diphosphate carboxylase small subunit which is induced by light irradiation (Fluhr, 1986, Proc. Natl. Acad. Sci. USA 83, 2358), a promoter for rice lip19 gene inducible by low temperature (Aguan, 1993, Mol. Gen. Genet. 240, 1), promoters for rice hsp72 and hsp80 genes inducible by high temperature (Van Breusegem, 1994, Planta 193, 57), a promoter for the rab16 gene of *Arabidopsis thaliana* inducible by dryness (Nundy, 1990, Proc. Natl. Acad. Sci. USA 87, 1406), and a promoter for maize alcohol dehydrogenase gene inducible by ultraviolet irradiation (Schulze-Lefert, 1989, EMBO J. 8, 651). A promoter for ther rab16 gene is inducible by spraying abscisic acid which is a plant hormone.

A "terminator" is a sequence which is located downstream of a region encoding a protein of a gene and which is involved in the termination of transcription when DNA is transcribed into mRNA, and the addition of a poly A sequence. It is known that a terminator contributes to the stability of mRNA, and has an influence on the amount of gene expression. Examples of such a terminator include, but are not limited to, a CaMV35S terminator and a terminator for the nopaline synthetase gene (Tnos).

A "drug-resistant gene" is desirably one that facilitates the selection of transformed plants. The neomycin phosphotransferase II (NPTII) gene for conferring kanamycin resistance, the hygromycin phosphotransferase gene for conferring hygromycin resistance, and the like may be preferably used. The present invention is not so limited.

An "enhancer" may be used so as to enhance the expression efficiency of a gene of interest. As such an enhancer, an enhancer region containing an upstream sequence within the CaMV35S promoter is preferable. A plurality of enhancers may be used.

Plant expression vectors as described above may be prepared using a gene recombination technique well known to those skilled in the art. In addition to vectors used in the Examples below, in construction of a plant expression vector, pBI vectors or pUC vectors are preferably used. The present invention is not so limited.

A plant material for DNA introduction can be appropriately selected from leaves, stems, roots, tubers, protoplasts, calluses, pollen, embryos, shoot primordium, according to the introduction method or the like. A "plant cell" may be any plant cell. Examples of a "plant cell" include cells of tissues in plant organs, such as leaves and roots; callus; and suspension culture cells. The plant cell may be in any form of a culture cell, a culture tissue, a culture organ, or a plant. Preferably, the plant cell is a culture cell, a culture tissue, or a culture organ. More preferably, the plant cell is a culture cell.

A plant culture cell, to which DNA is introduced, is generally a protoplast. DNA is introduced to a plant culture cell by a physicochemical method, such as an electroporation method and a polyethylene glycol method. A plant tissue, to which DNA is introduced, is a leaf, a stem, a root, a tuber, a callus, pollen, an embryo, shoot primordium, preferably a leaf, a stem, and a callus. DNA is introduced into a plant tissue by a physico chemical method, such as a biological method using a virus or Agrobacterium, or a particle gun method. The method using Agrobacterium is disclosed, for example, in Nagel et al. (Microbiol. Lett., 67, 325 (1990)). In this method, a plant expression vector is first used to transform Agrobacterium (e.g., by electroporation), and then the transformed Agrobacterium is introduced into a plant tissue by a well-known method, such as a leaf disc method. These methods are well known in the art. A method suitable for a plant to be transformed can be appropriately selected.

A cell, into which a plant expression vector has been introduced, is selected for drug resistance, such as kanamycin resistance. The selected cell can be regenerated to a plant by a commonly used method.

A plant cell, into which a polynucleotide of the present invention has been introduced, can be regenerated to a plant by culturing the plant cell in redifferentiation medium, hormone-free MS medium, or the like. A young rooted plant can be grown to a plant by transferring it to soil, followed by cultivation. Redifferentiation methods vary depending on the type of a plant cell. Redifferentiation methods for various plants are described: rice (Fujimura, 1995, Plant Tissue Culture Lett. 2, 74); maize (Shillito, 1989, Bio/Technol. 7, 581: Gorden-Kamm, 1990, Plant Cell 2, 603); potato (Visser, 1989, Theor. Appl. Genet. 78, 594); and tobacco (Nagata, 1971, Planta 99, 12).

Expression of an introduced gene of the present invention in a regenerated plant can be confirmed by a method well known to those skilled in the art. This confirmation can be carried out using, for example, Northern blotting. Specifically, total RNA is extracted from a plant leaf, is subjected to electrophoresis on denaturing agarose, and is blotted to an appropriate membrane. This blot is subjected to hybridization with a labeled RNA probe complementary to a portion of the introduced gene, thereby detecting mRNA of a gene of the present invention.

Plants which can be transformed using a polynucleotide of the present invention include any plant to which a gene can be introduced. As used herein, the term "plant" includes reference to whole plants, plant organs (e.g., leaves, stems, roots, etc.), seeds, plant propagators (e.g., pollen), and plant cells, and progeny of same. Plant cells as used herein include, without limitation, seeds, suspension cultures, embryos, meristematic regions, callus tissue, leaves, roots, shoots, gametophytes, sporophytes, pollen, and microspores. The term "plant" includes monocotyledonous and dicotyledonous plants. Such plants include any useful plants, particularly crop plants, vegetable plants, and flowering plants of garden varieties. Preferable plants include, but are not limited to, rice, maize, sorghum, barley, wheat, rye, *Echinochloa crus-galli*, foxtail millet, asparagus, potato, Japanese white radish, soybean, pea, rapeseed, spinach, tomato, and petunia. The most preferable plant to which the present invention is applied is rice, particularly Japonica rice.

Examples of types of plants that can be used in the manufacturing method of the present invention include plants in the families of Solanaceae, Poaeae, Brassicaceae, Rosaceae, Leguminosae, Curcurbitaceae, Lamiaceae, Liliaceae, Chenopodiaceae and Umbelliferae.

Examples of plants in the Solanaceae family include plants in the Nicotiana, Solanum, Datura, Lycopersicon and Petunia genera. Specific examples include tobacco, eggplant, potato, tomato, chili pepper, and petunia.

Examples of plants in the Poaeae family include plants in the *Oryza, Hordenum, Secale, Saccharum, Echinochloa* and *Zea* genera. Specific examples include rice, barley, rye, *Echinochloa crus-galli*, sorghum, and maize.

Examples of plants in the Brassicaceae family include plants in the *Raphanus, Brassica, Arabidopsis, Wasabia*, and *Capsella* genera. Specific examples include Japanese white radish, rapeseed, *Arabidopsis thaliana*, Japanese horseradish, and *Capsella bursa-pastoris*.

Examples of plants in the Rosaceae family include plants in the *Orunus, Malus, Pynus, Fragaria*, and *Rosa* genera. Specific examples include plum, peach, apple, pear, Dutch strawberry, and rose.

Examples of plants in the Leguminosae family include plants in the *Glycine, Vigna, Phaseolus, Pisum, Vicia, Arachis, Trifolium, Alfalfa*, and *Medicago* genera. Specific examples include soybean, adzuki bean, kidney bean, pea, fava bean, peanut, clover, and bur clover.

Examples of plants in the Curcurbitaceae family include plants in the *Luffa, Curcurbita*, and *Cucumis* genera. Specific examples include gourd, pumpkin, cucumber, and melon.

Examples of plants in the Lamiaceae family include plants in the *Lavandula, Mentha*, and *Perilla* genera. Specific examples include lavender, peppermint, and beefsteak plant.

Examples of plants in the Liliaceae family include plants in the *Allium, Lilium*, and *Tulipa* genera. Specific examples include onion, garlic, lily, and tulip.

Examples of plants in the Chenopodiaceae family include plants in the *Spinacia* genera. A specific example is spinach.

Examples of plants in the Umbelliferae family include plants in the *Angelica, Daucus, Cryptotaenia*, and *Apitum* genera. Specific examples include Japanese udo, carrot, honewort, and celery.

The nomenclature used hereafter and the laboratory procedures described hereafter often involve well known and commonly employed procedures in the art. Standard techniques are used for recombinant methods, polynucleotide synthesis, and cell culture. The techniques and procedures are generally performed according to conventional methods in the art and various general references (see, generally, Sambrook et al. Molecular Cloning: A Laboratory Manual, 2nd ed. (1989) Cold Spring Harbor Laboratory Press, Cold Spring Harbor, N.Y., which is incorporated herein by reference).

Hereinafter, the present invention will be described by way of examples. The present invention is not so limited. Materials, reagents, and the like used in the examples are available from commercial sources, unless otherwise mentioned.

EXAMPLES

Example 1

Activation of Tos17 by Culture and Characterization of Resultant Mutants

Mature seeds of "Nipponbare" (a variety of species Japonica) were used as starting material to conduct callus initiation culture and cell suspension culture, as described in Hirochika et al., 1996, Proc. Natl. Acad. Sci. USA, 93, 7783–7788) (supra). Culture conditions for activating Tos17 used in gene disruption were determined in accordance with Otsuki's method (1990) (Rice protoplast culture, Agriculture, Forestry and Fisheries Technical Information Society).

Briefly, mature seeds of rice were cultured in MS medium containing 2,4-Dichlorophenoxyacetic acid (2,4-D) (Otsuki (1990), supra) (25° C., 1 month) so as to induce calluses. The resultant calluses were cultured in N6 liquid medium-containing 2,4-D (Otsuki (1990), supra) for 5 months, and were transferred to redifferentiation medium (Otsuki (1990), supra) to obtain redifferentiated rice (first generation (R1) plant).

Figure 1:
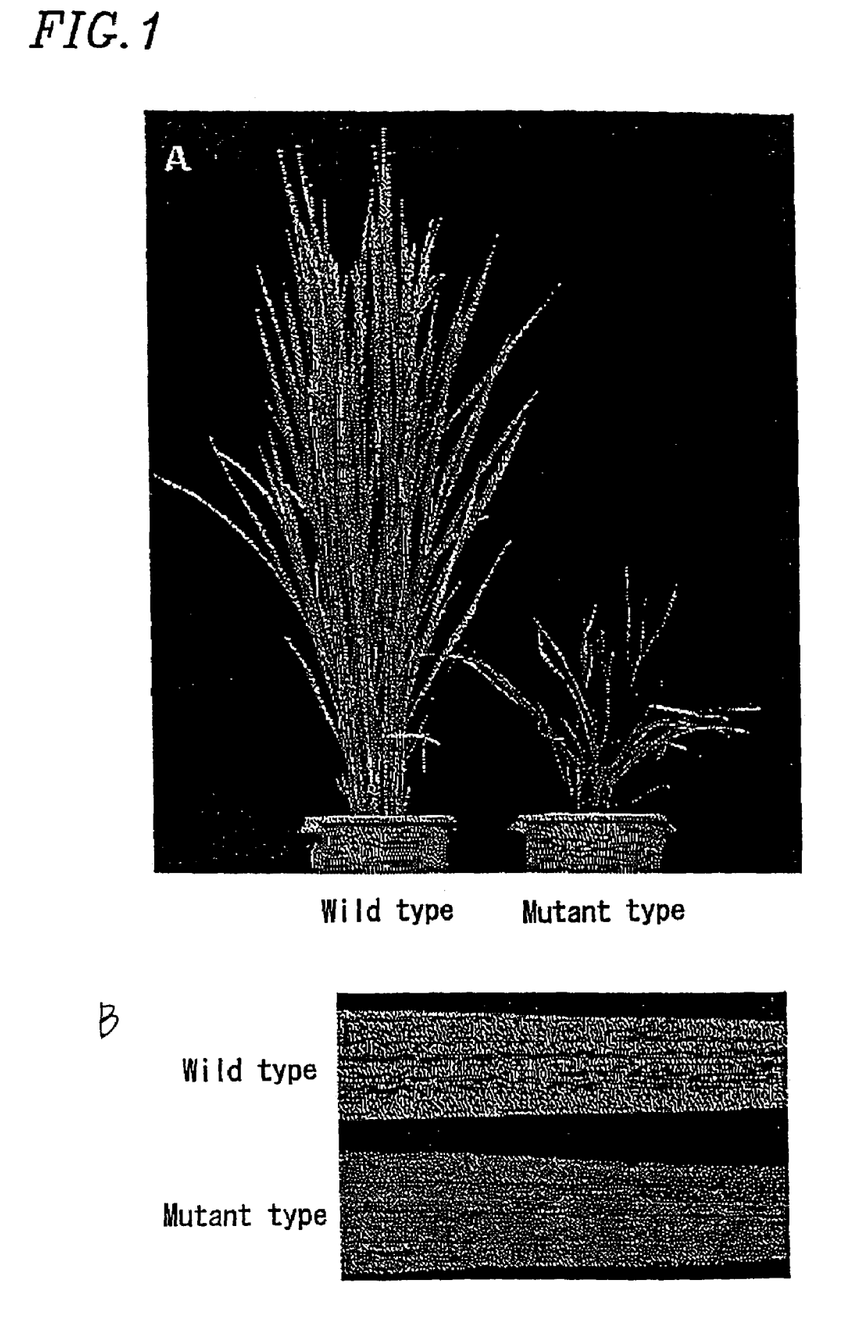
FIG. 1 shows photograph (A) indicating a lesion mimic mutant grown in a field and a control wild type, and photograph (B) indicating their leaves.

Seeds were recovered from the resultant R1 rice plants. The seeds were inoculated before they were transplanted to a field, to obtain second generation (R2) plants, which were then subjected to morphological analysis. The phenotypes of the plants of the R2 group were carefully monitored for 5 months after their germination. As a result, mutant strain ND5001 (variety Nipponbare) displaying mimic lesions (FIG. 1) was identified. FIG. 1 provides a photograph (A) showing lesion mimic mutants and a control wild type cultivated in the field, which are in the form of a shoot, and a photograph (B) showing their leaves. The wild type is shown to the left of photograph (A) and to the top of photograph (B), and the mutant is shown to the right of photograph (A) and to the bottom of photograph (B). In the lesion mimic mutants, brown spots began appearing on the leaves when five or six leaves developed. Thereafter, brown spots were also formed on newly developing leaves, and spread throughout each leaf blade, thereby wilting the mutant plants.

Example 2

Isolation of Flanking Sequence to Tos17

In order to find a gene which controls the phenotype observed in Example 1, a flanking sequence to Tos17, which had been transferred into genomic DNA, was isolated.

DNA was prepared from the R2 rice (strain ND5001) obtained in Example 1 by a CTAB method (Murray and Thompson, 1980, Nucleic Acids Res. 8, 4321–4325). A Tos17 target site sequence was amplified by TAIL-PCR (Liu Y-G. et al., Genomics, 25, 674–681; Liu Y-G. et al., 1995, Plant J., 8, 457–463) using total DNA.

Briefly, total DNA from a regenerated plant having an acquired Tos17 target site was used as an initial template to conduct amplification reactions by TAIL-PCR, where the three sets of primers below were employed. In the first PCR, the template DNA was the total DNA obtained above. As a Tos17 specific primer, Tail 3 (GAGAGCATCATCGGTTA-CATCTTCTC SEQ ID NO:3) was used. Tail 4 (ATCCAC-CTTGAGTTTGAAGGG SEQ ID NO:5) and Tail 5 (CATCGGATGTCCAGTCCATTG SEQ ID NO:6) were used in the second and third PCR, respectively. The first PCR was conducted using a total 20 μl of reaction solution. The sequence of the AD primer was NGTCGA(G/C)(A/T)GANA(A/T)GAA (SEQ ID NO:4) (AD1 primer). The AD primer was used as one of a PCR primer pair in the first to third PCR.

The final concentration and the number of cycles for the first PCR are described below.

(Final Concentration)
Template DNA; 0.5 ng/μL/tail 3 primer (Tos17 specific primer); 1 pmol/μL/AD primer; 10 pmol/μL/dNTP mix; 0.2 mM/10×PCR buffer (Applied Biosystems); 1×/Ex-Taq; 0.025 units/μL.

(The Number of Cycles)
95° C.·3 min/1 cycle, 94° C.·1 min-65° C.·1 min-72° C.·3 min/5 cycles, 94° C.·1 min-25° C.·3 min-72° C.·3 min/1 cycle, 94° C.·30 sec-68° C.·1 min-72° C.·3 min-94° C.·30 sec-68° C.·1 min-72° C. min-94° C.·30 sec-43° C.·1 min-72° C.·3 min/15 cycles, 72° C.·5 min/1 cycle, 4° C.·hold.

In the second PCR, 1/50 dilution of the first PCR solution was used as template DNA. The total amount of reaction solution was 20 μl. The final concentration and the number of cycles for the second PCR are described below.

(Final Concentration)
Template DNA/Tail 4 primer; 1 pmol/μL/AD primer; 10 pmol/μL/dNTP mix; 0.2 mM/10×PCR buffer (Applied Biosystems); 1×/Ex-Taq; 0.025 units/μL.

(The Number of Cycles)
95° C.·3 min/1 cycle, 94° C.·30 sec-64° C.·1 min-72° C.·3 min-94° C.·30 sec-64° C.·1 min-72° C.·3 min-94° C.·30 sec-43° C.·1 min-72° C. C.·min/12 cycles, 72° C.·5 min/1 cycle, 4° C.·hold.

In the third PCR 1/10 dilution of the second PCR solution was used as template DNA. The total amount of reaction solution was 50 μl. The final concentration and the number of cycles for the third PCR are described below.

(Final Concentration)
Template DNA/Tail 5 primer; 1 pmol/μL/AD primer; 10 pmol/μL/dNTP mix; 0.2 mM/10×PCR buffer (Applied Biosystems); 1×/Ex-Taq; 0.05 units/μL.

(The Number of Cycles)
95° C.·3 min/1 cycle, 94° C.·30 sec-66° C.·1 min-72° C.·30 sec-68° C.·1 min-72° C.·3 min-94° C.·30 sec-45° C.·1 min-72° C.·3 min/cycles, 72° C.·5 min/1 cycle, 4° C.·hold.

Next, TAIL-PCR products were subjected to agarose gel electrophoresis, followed by simple column purification. The purified products were directly sequenced using a sequencer (ABI, Model 3100).

Example 3

Structural Analysis of Causative Gene in Mutant

RNA was prepared from seedlings of wild type rice (Nipponbare) grown in soil for 11 days in the manner below. Initially, ISOGEN solution was used to extract total RNA from the seedlings. The total RNA was applied to an oligo(dt)cellulose column included in a mRNA purification kit (Stratagene) to obtain poly(A) mRNA. cDNA was synthesized from the resultant poly(A) mRNA by a commonly used method. A cDNA library was constructed in HybriZAP-2.1 vectors (Stratagene). The cDNA library had an infection ability of 5×10⁵ plaques. In vivo cleavage of pBluescript plasmid including cDNA inserted fragments was conducted using Escherichia coli strain XL1-Blue MRF2.

The cDNA library was subjected to screening in accordance with a method described in Molecular Cloning, A Laboratory Manual (Sambrook et al., 1989), where the TAIL-PCR products of the flanking sequence to Tos17, which were obtained in Example 2, were used as probes.

From the cDNA library, 5 cDNA clones exhibiting a strong hybridization signal were obtained.

The longest cDNA having a size of about 1.4 kb of the clones was sequenced using the sequencer 3100 (Applied Biosystems (ABI)) in both directions, followed by homology analysis using open reading frame (ORF) and BLAST was analyzed by extracting RNA from mutant rice and wild type rice, followed by Northern blotting.

Plants were germinated under water for 7 days, and were transplanted to soil, followed by cultivation for 2, 4 and 6 weeks. From leaves of the plants, total RNA was extracted using ISOGEN RNA extraction solution (Nippongene), and was subjected to separation using 1.5% agarose gel containing 5% (v/v) formaldehyde solution. For the electrophoresis, about 10 μg of RNA was used. A pathogenesis-related protein 1b (PR1b) and phenylalanine ammonialyase (PAL), which are a defense-related gene expressed in disease resistance reactions, were used as hybridization probes in a hybridization solution containing 0.5 M NaH$_2$PO$_4$—Na$_2$HPO$_4$ (pH 7.2), 7% SDS, 200 μg of calf thymus DNA at 68° C. for 3 and 12 hours in accordance with a method described in Sambrook et al., 1989 (supra). The probe sequences are described below.

```
<PAL>:
CCATCCCCTGAGATTCATGGGCTGTTCCTACTCTTTATTAGCAAAAGAAAAAAA     (SEQ ID NO:7)

CAGAAGCAAATAAATGCACTCCCTTACCAGCATGGAATTTTTTGCTCATAGCAT

AAAGTCAAGTACAGCATCCAAGCTGTTTAATTCTAGTACAAGCTGGAAAACTTG

TCTCATGTGTAGTATATACACCACCAGCACAGCTCCAGTTGAAAAAAAAAAAGA

AAAAAACGGCCA

<PR1b>:
AATTCTATGTCCAAGTGCATACTTTGCGGGGGTAAAATTTTCTACACGTATGTT     (SEQ ID NO:8)

GCCAAAATTTCTGCTAAGTTTTCGTGCCAACTCGAGAAATTCTTACACAGCCTG

CAGTCTATAAATATTCACACATTTCACAAAAAAATACTTGCAACATCAAAGCTAC

ACAGGTAGAATCATCGACCGTAAGTAGGTACGTACATTAAGTGTGAGCTTGATT

AACTATGGAGGTATCCAAGCTGG
```

(Altshul et al., 1997, Nucleic Acids Res., 25, 3389–3402) and analysis using Mac Vector 6.0 program (Teijin System Technology).

Figure 3:
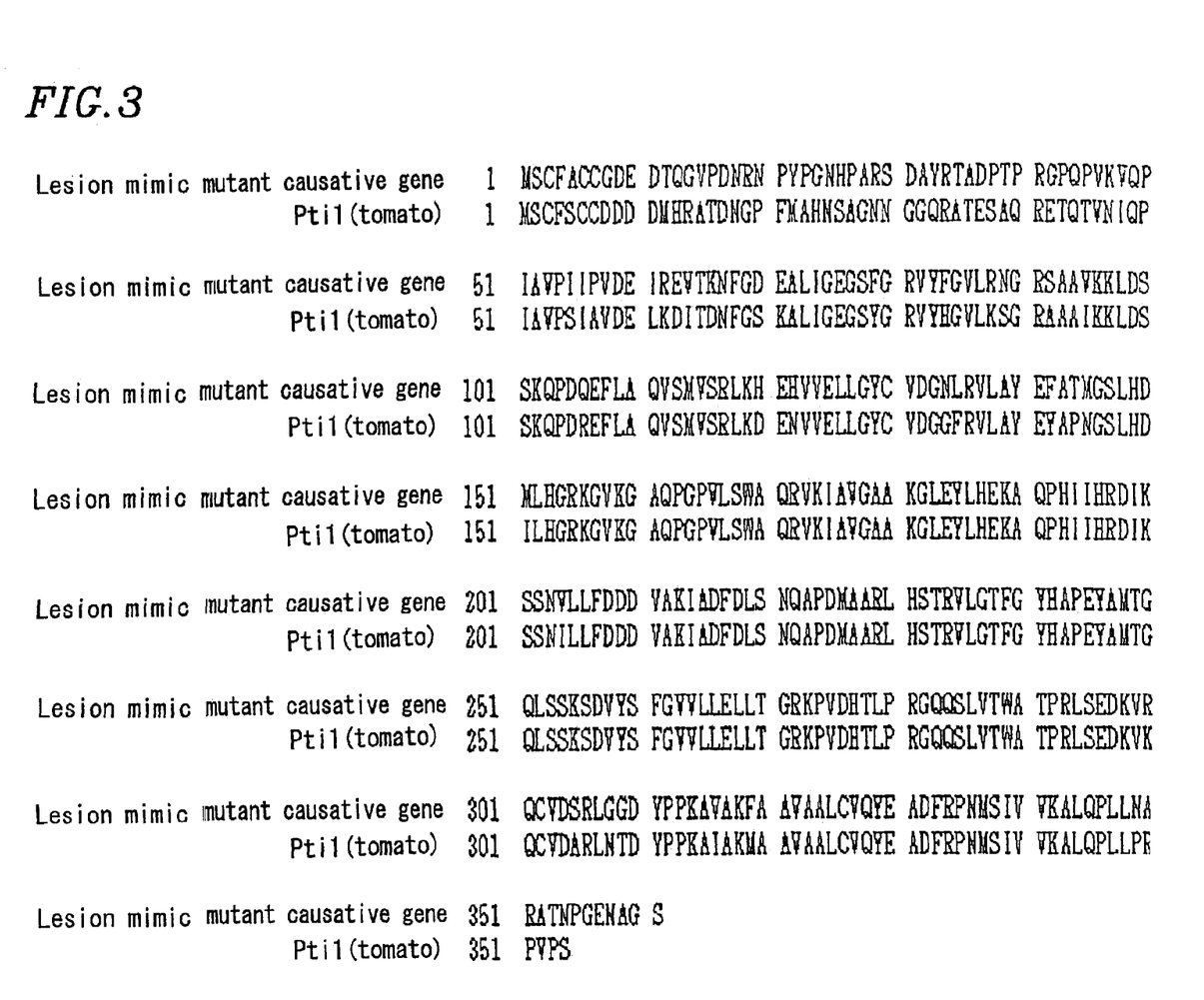
FIG. 3 is a diagram showing comparison of amino acid sequence between a protein encoded by the lesion mimic mutant causative gene (SEQ ID NO:2) and tomato Pti1 (SEQ ID NO:9).

According to the sequencing analysis, the longest cDNA clone was 1395 bp in length (SEQ ID NO: 1). The mRNA analysis using the Mac Vector 6.0 package identified the longest open reading frame of 1083 bp encoding a protein consisting of 361 amino acids (SEQ ID NO: 2). The cDNA sequence of 1395 bp indicated by SEQ ID NO: 1 is shown in FIG. 2. The open reading frame is located at position 146–1231of the cDNA sequence. A putative amino acid sequence (SEQ ID NO: 2) of a polypeptide encoded by the open reading frame is shown in FIG. 3. As a result of the amino acid sequence analysis, it is inferred that the protein has a kinase domain. The protein also has a high level of amino acid sequence homology to Pto kinase interactor 1 (Pti1) which is a tomato disease resistance related gene (84%). The comparison between the sequences of the two proteins is shown in FIG. 3. The homology was determined by homology analysis using BLAST (Altshul et al., 1997, Nucleic Acids Res., 25, 3389–3402). It is known that tomato Pti1 has a function of accelerating disease resistance reactions involved with the Pto resistance gene.

Example 4

Evaluation of Induction of Disease Resistance in Lesion Mimic Mutant

The expression inhibition of a causative gene of the lesion mimic mutant due to the insertion of Tos17 into the gene, After hybridization, a filter was washed at 55° C. with 2×SSC solution containing 0.5% SDS two times for a total of 1 hour.

Figure 4:
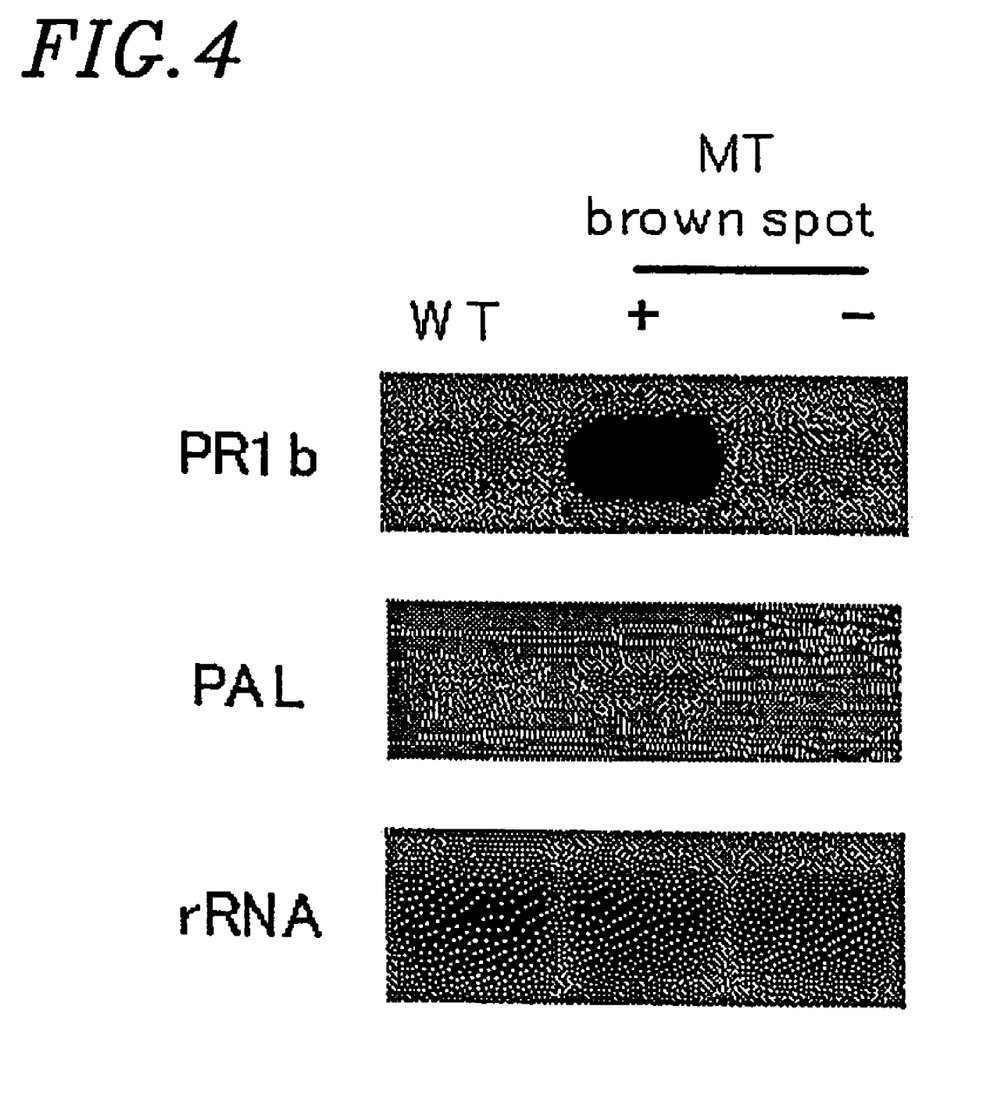
FIG. 4 is an electrophoresis photograph showing analysis of expression of a defense-related gene in the lesion mimic mutant.

By Northern blot analysis, it was found that PR1b and PAL were expressed in leaves of the mutant plant having brown spots. The results are shown in FIG. 4. PR1b, PAL, and ribosomal RNA are indicated in this order from the top. In each lane, the left portion indicates a wild type (WT), the middle and right portion indicate a mutant type (MT). The middle portion indicates the case when brown spots were present (brown spot (+)), and the right portion indicates the case when substantially no brown spots were present (brown spot (−)). Expression of the defense-related gene was confirmed in leaves having brown spots.

Phytoalexins (momilactone A and sakuranetin) were quantified in leaves of the lesion mimic mutants. The quantification was conducted in accordance with a method described in Takahashi et al., Plant J. (1999) 17, 535–545. Briefly, tissue including lesion spots (diameter: 5 mm) was subjected to extraction using 5 ml of 80% methanol, followed by boiling. Thereafter, 10 ml of brine was added to the methanol solution, and phytoalexin was extracted using 5 ml of EtOAc (3 times). After drying with Na$_2$SO$_4$, the EtOAc layer was concentrated in vacuum to obtain a crude extract. The extract was dissolved in 3 ml of n-hexane, and the mixture was loaded onto Sep-Pak Light Silica Cartilage. The eluate was diluted with 2 ml of MeOH, followed by analysis using a LC/MS/MS system. LC conditions: column Inertsil ODS 2; solvent, CH$_3$CN containing 0.1% formic acid; flow rate, 0.5 ml/min. In this analysis, momilactone A and sakuranetin were used as standard substances. The results are shown in Table 1.

TABLE 1

Phytoalexin content in leaves of lesion mimic mutant strain

|  | Momilactone A (µg/g fresh weight) | Sakuranetin (µg/g fresh weight) |
|---|---|---|
| Mutant 1 (with brown spot) | 28.94 | 0.39 |
| Mutant 2 (with brown spot) | 24.31 | 0.35 |
| Mutant 3 (with brown spot) | 18.19 | 2.98 |
| Mutant 1 (without brown spot) | n/d | n/d |
| Mutant 2 (without brown spot) | n/d | n/d |
| Wild type 1 | n/d | n/d |
| Wild type 2 | n/d | n/d |
| Wild type 3 | n/d | n/d |

Table 1 shows the phytoalexin (momilactone A and sakuranetin) content (µg) per g fresh weight of leaves, where n/d indicates substantially no detection.

According to Table 1, it is found that momilactone A is particularly accumulated in brown spotted leaves of mutants.

According to the above-described results, it was revealed that the causative gene of the lesion mimic mutant negatively controls the induction of disease resistance reactions. It was thus found that the gene has a function contrary to the function of tomato Pti1 to accelerate the disease resistance reaction involved with the Pto resistance gene.

Example 5

Complementarity Test of Lesion Mimic Mutant

Construction of Complementary Vector and Transformation of Lesion Mimic Mutant Using *Agrobacterium Tumefaciens* cDNA of about 1.4 kb containing an open reading frame of the full-length of the above-described gene was linked downstream of the CaMV35S promoter, and was incorporated into pPZP2Ha3(+) vector (Fuse et al., Plant Biotechnology, 18, 219–222). *Agrobacterium tumefaciens* EHA101 was transformed by electroporation using the recombinant vector in the presence of 50 mg/l kanamycin and hygromycin. The resultant *Agrobacterium* strain was cryopreserved before use.

Seeds of the above-described gene mutant were sterilized with 1% sodium hypochlorite, followed by washing with sterilized distilled water 5 times. These seeds were subjected to transformation in accordance with a method described in JP No. 3141084 granted to Tanaka et al. After removal of the chaff, the intact seeds were sterilized in 2.5% sodium hypochlorite (NaClO) solution, followed by thorough washing with water. Thereafter, the seed was subjected to aseptic manipulation.

Thereafter, the seeds were inoculated in N6D medium (30 g/l sucrose, 0.3 g/l casamino acid, 2.8 g/l proline, 2 mg/l 2,4-D, 4 g/l gelrite, pH 5.8) containing 2,4-D, followed by incubation at 27° C. to 32° C. for 5 days. During the incubation, the seeds sprouted.

The cultured seeds were immersed in a suspension solution containing the transformed *Agrobacterium*, and thereafter, were transferred to 2N6-AS medium(30 g/l sucrose, 10 g/l glucose, 0.3 g/l casamino acid, 2 mg/l 2,4-D, 10 mg/l acetosyringone, 4 g/l gelrite, pH 5.2). The cocultivation was conducted in a dark place at 28° C. for 3 days.

After cocultivation, the *Agrobacterium* was washed out using N6D medium containing 500 mg/l carbenicillin. Thereafter, screening for the transformed seeds was conducted under the following conditions.

First screening: the seeds were placed on N6D medium containing 2 mg/l 2,4-D supplemented with carbenicillin (500 mg/l) and hygromycin (25 mg/l), followed by incubation at 27° C. to 32° C. for 7 days.

Second screening: the seeds were placed on N6D medium containing 2 to 4 mg/l 2,4-D supplemented with carbenicillin (500 mg/l) and hygromycin (25 mg/l), followed by incubation at 27° C. to 32° C. for 7 days.

The selected, transformed seeds were subjected to redifferentiation under the following conditions.

First redifferentiation: the selected seeds were placed on redifferentiation medium, which was MS medium (30 g/l sucrose, 30 g/l sorbitol, 2 g/l casamino acid, 2 mg/l kinetin, 0.002 mg/l NAA, 4 g/l gelrite, pH 5.8) supplemented with carbenicillin (500 mg/l) and hygromycin (25 mg/l), followed by incubation at 27° C. to 32° C. for 2 weeks.

Second redifferentiation: the same redifferentiation medium as that in the first redifferentiation was used for further incubation at 27° C. to 32° C. for 2 weeks.

A redifferentiated transformant was transferred to rooting medium (hormone-free MS medium containing hygromycin (25 mg/l)). After confirmation of growth of root, the transformant was potted. The transformant did not develop brown spot, exhibiting a phenotype similar to the wild type. As a result, it was demonstrated that the mutation of the above-described gene is the cause of lesion mimic mutation.

The present invention provides a novel polynucleotide capable of controlling disease resistance reactions, which can be used for plant breeding. The present invention also provides a polynucleotide useful for producing a plant whose disease resistance against various pathogens is enhanced.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. An isolated polynucleotide encoding polypeptide comprising the amino acid sequence of SEQ ID NO: 2.

2. An isolated polynucleotide comprising the nucleotide sequence SEQ ID NO: 1.

3. A vector comprising the isolated polynucleotide according to claim 1, wherein the polynucleotide is operably linked to a regulatory sequence.

4. A method for controlling disease resistance in a plant, comprising introducing a polynucleotide encoding a polypeptide comprising the amino acid sequence of SEQ ID NO:2 into the plant.

5. A vector comprising the isolated polynucleotide according to claim 2, wherein the polynucleotide is operably linked to a regulatory sequence.

6. A method for controlling disease resistance in a plant, comprising:
introducing the polynucleotide according to claim 2 into the plant.

7. A transgenic plant comprising the vector of claim 3.

8. A transgenic plant comprising the vector of claim 5.

9. A transgenic plant produced by the method of claim 4.

10. A transgenic plant produced by the method of claim 6.

11. A method for controlling disease resistance in a plant, comprising introducing the vector of claim 3 into the plant.

12. A method for controlling disease resistance in a plant, comprising introducing the vector of claim 5 into the plant.

* * * * *

SEQUENCE LISTING

<160> NUMBER OF SEQ ID NOS: 8

<210> SEQ ID NO 1
<211> LENGTH: 1395

<212> TYPE: DNA
<213> ORGANISM: Oryza sativa
<220> FEATURE:
<221> NAME/KEY: CDS
<222> LOCATION: (146)..(1231)
<223> OTHER INFORMATION:

<400> SEQUENCE: 1

```
acacacgctg tgctgctgct gctgccgctg ctcctcctcc tcctcttaca tcccatcctc    60
gccgcgattt ccttcgccgc cgccgccggc ttcgtcttct tccccggcgc cggggcacgc   120
gaaaagggtt tgtttctagt agaat atg tcg tgc ttt gca tgc tgt ggt gat     172
                           Met Ser Cys Phe Ala Cys Cys Gly Asp
                             1               5 gaa gat act caa gga gta cca gac aac agg aat cca tac cca ggg aac    220
Glu Asp Thr Gln Gly Val Pro Asp Asn Arg Asn Pro Tyr Pro Gly Asn
 10              15                  20                  25 cat cca gca agg agc gat gca tat cgc aca gct gat cca act cca aga   268
His Pro Ala Arg Ser Asp Ala Tyr Arg Thr Ala Asp Pro Thr Pro Arg
                 30                  35                  40 ggt cct caa cct gtg aaa gtg caa cca att gca gtc ccc atc att cct   316
Gly Pro Gln Pro Val Lys Val Gln Pro Ile Ala Val Pro Ile Ile Pro
             45                  50                  55 gtt gat gaa att agg gaa gtg act aag aat ttt ggt gat gaa gct ttg   364
Val Asp Glu Ile Arg Glu Val Thr Lys Asn Phe Gly Asp Glu Ala Leu
         60                  65                  70 att ggt gaa ggt tcc ttt ggc aga gtg tat ttt ggt gtt cta aga aat   412
Ile Gly Glu Gly Ser Phe Gly Arg Val Tyr Phe Gly Val Leu Arg Asn
     75                  80                  85 ggt aga agt gca gcg gtc aaa aag cta gac tct agt aag cag cca gac   460
Gly Arg Ser Ala Ala Val Lys Lys Leu Asp Ser Ser Lys Gln Pro Asp
 90                  95                 100                 105 caa gaa ttt ttg gca cag gta tct atg gtg tcg agg ctt aag cat gaa   508
Gln Glu Phe Leu Ala Gln Val Ser Met Val Ser Arg Leu Lys His Glu
                110                 115                 120 cat gtt gtt gag ctg ctt ggt tat tgt gtt gat gga aat ctc cgt gtc   556
His Val Val Glu Leu Leu Gly Tyr Cys Val Asp Gly Asn Leu Arg Val
            125                 130                 135 ctt gct tat gag ttt gcg act atg ggt tct ctt cat gat atg ctt cat   604
Leu Ala Tyr Glu Phe Ala Thr Met Gly Ser Leu His Asp Met Leu His
        140                 145                 150 gga agg aag ggt gtt aaa gga gct caa cct ggt cca gtc tta tca tgg   652
Gly Arg Lys Gly Val Lys Gly Ala Gln Pro Gly Pro Val Leu Ser Trp
    155                 160                 165 gca caa cgt gtg aag ata gct gtt ggg gca gca aaa ggc ctg gag tat   700
Ala Gln Arg Val Lys Ile Ala Val Gly Ala Ala Lys Gly Leu Glu Tyr
170                 175                 180                 185 ctt cat gag aaa gca cag cct cat atc ata cac agg gac atc aag tcc   748
Leu His Glu Lys Ala Gln Pro His Ile Ile His Arg Asp Ile Lys Ser
                190                 195                 200 agc aat gtt ctc ctt ttc gat gat gat gtt gct aaa ata gct gac ttt   796
Ser Asn Val Leu Leu Phe Asp Asp Asp Val Ala Lys Ile Ala Asp Phe
            205                 210                 215 gat ttg tca aac caa gct cct gac atg gca gct cgg ctt cac tct act   844
Asp Leu Ser Asn Gln Ala Pro Asp Met Ala Ala Arg Leu His Ser Thr
        220                 225                 230 agg gtt ctt gga acc ttt gga tat cat gca cct gag tat gca atg act   892
Arg Val Leu Gly Thr Phe Gly Tyr His Ala Pro Glu Tyr Ala Met Thr
    235                 240                 245 gga cag ctt agc tcc aag agt gat gtg tac agt ttt gga gtt gtt ctt   940
Gly Gln Leu Ser Ser Lys Ser Asp Val Tyr Ser Phe Gly Val Val Leu
```

-continued

```
             250                 255                 260                 265
ctt gag cta ttg acc gga agg aaa cct gtt gac cat aca tta cca agg          988
Leu Glu Leu Leu Thr Gly Arg Lys Pro Val Asp His Thr Leu Pro Arg
                    270                 275                 280 gga cag cag agt ctt gtg act tgg gcc acc cca agg ctt agt gaa gac         1036
Gly Gln Gln Ser Leu Val Thr Trp Ala Thr Pro Arg Leu Ser Glu Asp
                285                 290                 295 aag gtt agg caa tgt gtt gac tca aga ctt gga ggg gac tat cct cct         1084
Lys Val Arg Gln Cys Val Asp Ser Arg Leu Gly Gly Asp Tyr Pro Pro
            300                 305                 310 aaa gct gtc gca aag ttt gca gct gtt gcg gcg tta tgc gtt cag tat         1132
Lys Ala Val Ala Lys Phe Ala Ala Val Ala Ala Leu Cys Val Gln Tyr
        315                 320                 325 gaa gcg gac ttt cga cca aac atg agc att gtc gtg aaa gcg ctg caa         1180
Glu Ala Asp Phe Arg Pro Asn Met Ser Ile Val Val Lys Ala Leu Gln
330                 335                 340                 345 ccc ctg ctg aat gct cgg gca act aac cct gga gaa aat gcc ggg tca         1228
Pro Leu Leu Asn Ala Arg Ala Thr Asn Pro Gly Glu Asn Ala Gly Ser
                350                 355                 360 taa aactttggtc tacctttttgt atgatagata ttaagttaag aagtatgaga             1281
catcgatatt gttcttgcgg atgtgtggct ggctggaagt gtgtacattt gtgattattc       1341
gtcccttgtt gtaatcacca aggttctagc aaccgaaaat atttgattct tcgc             1395
```

<210> SEQ ID NO 2
<211> LENGTH: 361
<212> TYPE: PRT
<213> ORGANISM: Oryza sativa

<400> SEQUENCE: 2

```
Met Ser Cys Phe Ala Cys Cys Gly Asp Glu Asp Thr Gln Gly Val Pro
1               5                   10                  15

Asp Asn Arg Asn Pro Tyr Pro Gly Asn His Pro Ala Arg Ser Asp Ala
            20                  25                  30

Tyr Arg Thr Ala Asp Pro Thr Pro Arg Gly Pro Gln Pro Val Lys Val
        35                  40                  45

Gln Pro Ile Ala Val Pro Ile Ile Pro Val Asp Glu Ile Arg Glu Val
    50                  55                  60

Thr Lys Asn Phe Gly Asp Glu Ala Leu Ile Gly Glu Gly Ser Phe Gly
65                  70                  75                  80

Arg Val Tyr Phe Gly Val Leu Arg Asn Gly Arg Ser Ala Ala Val Lys
                85                  90                  95

Lys Leu Asp Ser Ser Lys Gln Pro Asp Gln Glu Phe Leu Ala Gln Val
            100                 105                 110

Ser Met Val Ser Arg Leu Lys His Glu His Val Val Glu Leu Leu Gly
        115                 120                 125

Tyr Cys Val Asp Gly Asn Leu Arg Val Leu Ala Tyr Glu Phe Ala Thr
    130                 135                 140

Met Gly Ser Leu His Asp Met Leu His Gly Arg Lys Gly Val Lys Gly
145                 150                 155                 160

Ala Gln Pro Gly Pro Val Leu Ser Trp Ala Gln Arg Val Lys Ile Ala
                165                 170                 175

Val Gly Ala Ala Lys Gly Leu Glu Tyr Leu His Glu Lys Ala Gln Pro
            180                 185                 190

His Ile Ile His Arg Asp Ile Lys Ser Ser Asn Val Leu Leu Phe Asp
        195                 200                 205
```

```
Asp Asp Val Ala Lys Ile Ala Asp Phe Asp Leu Ser Asn Gln Ala Pro
    210                 215                 220
Asp Met Ala Ala Arg Leu His Ser Thr Arg Val Leu Gly Thr Phe Gly
225                 230                 235                 240
Tyr His Ala Pro Glu Tyr Ala Met Thr Gly Gln Leu Ser Ser Lys Ser
                245                 250                 255
Asp Val Tyr Ser Phe Gly Val Val Leu Glu Leu Leu Thr Gly Arg
                260                 265                 270
Lys Pro Val Asp His Thr Leu Pro Arg Gly Gln Gln Ser Leu Val Thr
                275                 280                 285
Trp Ala Thr Pro Arg Leu Ser Glu Asp Lys Val Arg Gln Cys Val Asp
    290                 295                 300
Ser Arg Leu Gly Gly Asp Tyr Pro Pro Lys Ala Val Ala Lys Phe Ala
305                 310                 315                 320
Ala Val Ala Ala Leu Cys Val Gln Tyr Glu Ala Asp Phe Arg Pro Asn
                325                 330                 335
Met Ser Ile Val Val Lys Ala Leu Gln Pro Leu Leu Asn Ala Arg Ala
                340                 345                 350
Thr Asn Pro Gly Glu Asn Ala Gly Ser
                355                 360
```

```
<210> SEQ ID NO 3
<211> LENGTH: 26
<212> TYPE: DNA
<213> ORGANISM: Artificial Sequence
<220> FEATURE:
<223> OTHER INFORMATION: Tos17 Tail3 primer

<400> SEQUENCE: 3
gagagcatca tcggttacat cttctc                                      26

<210> SEQ ID NO 4
<211> LENGTH: 16
<212> TYPE: DNA
<213> ORGANISM: Artificial Sequence
<220> FEATURE:
<223> OTHER INFORMATION: AD1 primer
<220> FEATURE:
<221> NAME/KEY: misc_feature
<222> LOCATION: (1)..(1)
<223> OTHER INFORMATION: n = a, t, c or g
<220> FEATURE:
<221> NAME/KEY: misc_feature
<222> LOCATION: (11)..(11)
<223> OTHER INFORMATION: n = a, t, c or g

<400> SEQUENCE: 4
ngtcgaswga nawgaa                                                 16

<210> SEQ ID NO 5
<211> LENGTH: 21
<212> TYPE: DNA
<213> ORGANISM: Artificial Sequence
<220> FEATURE:
<223> OTHER INFORMATION: Tos17 Tail4 primer

<400> SEQUENCE: 5
atccaccttg agtttgaagg g                                           21

<210> SEQ ID NO 6
<211> LENGTH: 21
<212> TYPE: DNA
<213> ORGANISM: Artificial Sequence
```

```
-continued

<220> FEATURE:
<223> OTHER INFORMATION: Tos17 Tail5 primer

<400> SEQUENCE: 6
catcggatgt ccagtccatt g                                              21

<210> SEQ ID NO 7
<211> LENGTH: 228
<212> TYPE: DNA
<213> ORGANISM: Artificial Sequence
<220> FEATURE:
<223> OTHER INFORMATION: PAL probe

<400> SEQUENCE: 7
ccatcccctg agattcatgg gctgttccta ctctttatta gcaaaagaaa aaaacagaag     60
caaataaatg cactccctta ccagcatgga attttttgct catagcataa agtcaagtac    120
agcatccaag ctgtttaatt ctagtacaag ctggaaaact tgtctcatgt gtagtatata    180
caccaccagc acagctccag ttgaaaaaaa aaagaaaaa acggcca                   228

<210> SEQ ID NO 8
<211> LENGTH: 240
<212> TYPE: DNA
<213> ORGANISM: Artificial Sequence
<220> FEATURE:
<223> OTHER INFORMATION: PR1b probe

<400> SEQUENCE: 8
aattctatgt ccaagtgcat actttgcggg ggtaaaattt tctacacgta tgttgccaaa     60
atttctgcta agttttcgtg ccaactcgag aaattcttac acagcctgca gtctataaat    120
attcacacat ttcacaaaaa aatacttgca acatcaaagc tacacaggta gaatcatcga    180
ccgtaagtag gtacgtacat taagtgtgag cttgattaac tatggaggta tccaagctgg    240
```